United States Patent [19]

Chaleff et al.

[11] Patent Number: 4,774,381

[45] Date of Patent: * Sep. 27, 1988

[54] HERBICIDE RESISTANT TOBACCO

[75] Inventors: Roy S. Chaleff; Thomas B. Ray, both of Wilmington, Del.

[73] Assignee: E. I. Du Pont de Nemours and Company, Wilmington, Del.

[*] Notice: The portion of the term of this patent subsequent to Jul. 12, 2005 has been disclaimed.

[21] Appl. No.: 747,099

[22] Filed: Jun. 20, 1985

Related U.S. Application Data

[63] Continuation of Ser. No. 537,560, Sep. 30, 1983.

[51] Int. Cl.$^4$ .......................... A01H 1/04; A01H 1/00; C12N 15/00; C12N 5/00; C07H 15/12

[52] U.S. Cl. ..................................... 800/1; 435/172.1; 435/240.4; 935/14; 536/27; 47/58

[58] Field of Search .................... 47/58; 435/240, 241, 435/172.1; 536/27; 800/1

Primary Examiner—Charles F. Warren
Assistant Examiner—David Fox

[57] ABSTRACT

Tobacco varieties exhibiting agronomically useful resistance to N-(heterocyclicaminocarbonyl)arylsulfonamide herbicides are produced by tissue culture selection techniques.

21 Claims, 2 Drawing Sheets

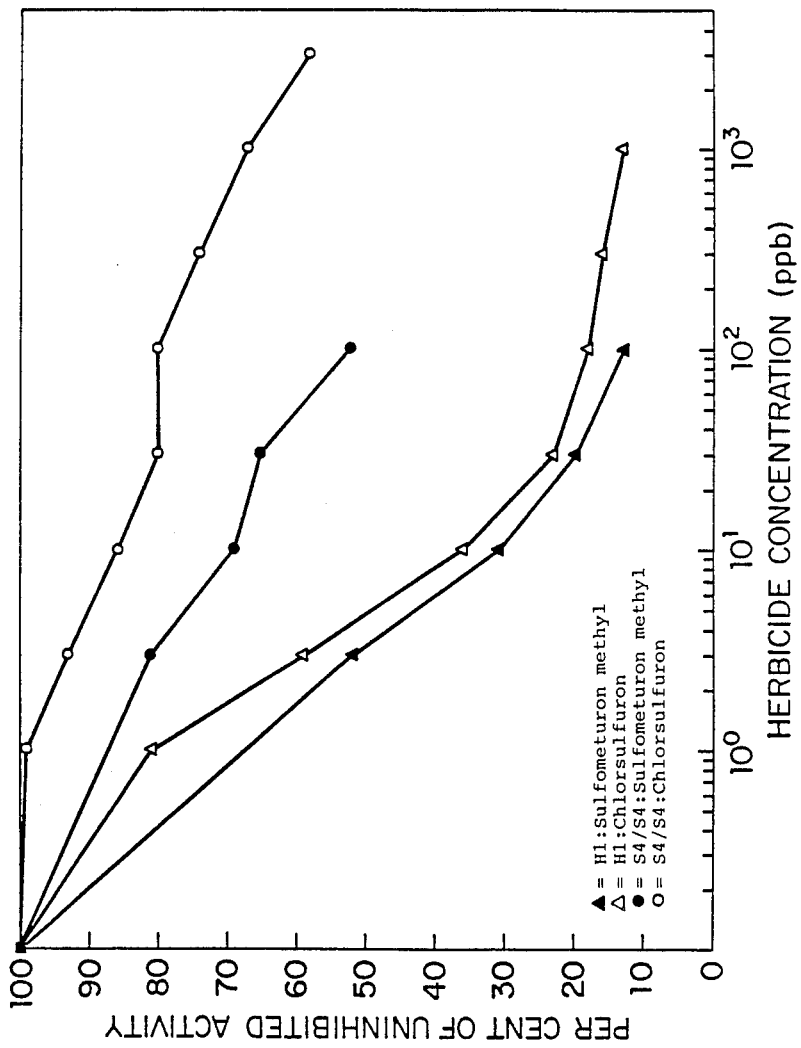

HERBICIDE RESISTANT TOBACCO

CROSS REFERENCE TO RELATED APPLICATION

This application is a continuation of U.S. application Ser. No. 537,560, now allowed.

BACKGROUND OF THE INVENTION

This invention relates to mutant tobacco plants having agronomically useful genetic resistace to certain broad-spectrum herbicides.

Chaleff, *Science* 219:676 (1983) discusses methods of isolating plant mutants from tissue culture under selective growth conditions. These methods have been applied to several crop species, but the majority of novel phenotypes reported to date are of limited practical utility. These results can be attributed to the genetic and developmental complexity of agriculturally important characteristics. Many traits are exclusively whole plant functions which are not expressed at the cellular level, and thus cannot be detected by an in-vitro selection procedure.

Herbicide resistance resulting from alterations of basic metabolic functions is a trait which can be expressed by isolated plant cells in culture, since herbicides that inhibit such functions can be expected to inhibit growth of cultured cells as well as developed plants. Chaleff, et al., *Proc. Nat. Acad. Sci. U.S.A.* 75:5104–5107 (1978) describe isolation of tobaco mutants exhibiting increased tolerance to picloram (4-amino-3,5,6-trichloropicolinic acid), a systemic herbicide. Picloram tolerance was expressed by regenerated plants and transmitted to progeny as a dominant or semidominant nuclear allele. Seeds derived from picloram-tolerant mutants germinated in the presence of 100 $\mu$M picloram. However, development beyond the seedling stage was not observed. After one month's exposure to 50 $\mu$M picloram, plantlets homozygous for tolerance mutations developed stem callus tissue and degenerated. However, the effect of picloram on soil-grown picloram-tolerant strains was not determined.

Miller, et al., *In-Vitro* 16:1085–1091 (1980) describe isolation of paraquat-resistant cell lines from cell cultures of *Nicotiana tabacum*. Plants were regenerated from resistant callus cultures, but no breeding experiments were conducted to study inheritance of the paraquat resistance trait. In any event, the resistance reported was a short-lived phenomenon. In these experiment plants were considered "resistant" if leaves required 4-7 days to bleach to white at paraquat concentrations of $10^{-5}$ M, versus an average of 3.5 days for controls. The authors concluded that several forms of paraquat resistance could be detected in vitro, not all of which were expressed by intact plants.

Singer, et al., *Plant Physiol.* 69:573 (1982) describe isolation and regeneration of tobacco plants exhibiting tolerance to amitrole (3-amino-1,2,4-triazole) and glyphosate (N-phosphonomethyl glycine). For the majority of isolates, tolerance was diminished or eliminated after lengthy passages away from herbicide. In the few cases in which inheritance of tolerace was observed, Singer, et al., described the patterns of such inheritance as "complex."

Thomas, et al., *Theor. Appl Genet.* 63:169–176 (1982) describe isolation of paraquat-tolerant mutants from tomato cell cultures. Diploid plants were regenerated from several of the paraquat-tolerant clones. Some of the plants appeared normal, but others had altered morphology and reduced vigor and fertility.

The potential of in-vitro selection techniques for development of herbicide-resistant crop varieties has bee highlighted by Knopf, *J. Theor. Biol.* 94:985 (1982). Knopf proposes a "plant for the herbicide" concept, involving development of crop varieties specifically resistant to a selected herbicidal compound with "ideal" characteristics. Such a compound should exhibit a wide spectrum of effectiveness at low rates of application, in combination with low animal toxicity.

Many N-(heterocyclicaminocarbonyl)arylsulfonamides exhibit very potent, broad-spectrum herbicidal activities and low mammalian toxicities. Exemplary of this class of herbicides are chlorsulfuron and sulfometuron-methyl, the active ingredients of the Du Pont herbidies Glean ® and Oust ®, respectively.

Accordingly, a principal object of the present invention is to provide mutant strains of *Nicotiana tabacum* with agronomically useful resistance to herbicidal sulfonamide compounds. A further object is to provide methods of obtaining the mutant strains. Such mutants should be stable with respect to the resistance phenotype throughout the plant life cycle, and be capable of genetically transmitting the resistance trait to progeny in predictable fashion, enabling integration of the resistance trait into commercial varieties by means of breeding programs.

SUMMARY OF THE INVENTION

The present invention provides mutant *Nicotiana tabacum* plants having stable heritable resistance to N-(heterocyclicaminocarbonyl)arylsulfonamide herbicides, which resistance is attributable to expression of an altered acetolactate synthase enzyme which is insensitive to inhibition by such herbicides. The present invention also provides a mutant *Nicotiana tabacum* gene, the presence of which in a *Nicotiana tabacum* plant permits expression of an altered acetolactate synthase enzyme which is insensitive to inhibition by N-(heterocyclicaminocarbonyl)arylsulfonamide herbicides. The plants of the present invention are produced by a process comprising propagating cell cultures of *N.tabacum* under plant tissue culture conditions; exposing the cell cultures to a selective medium comprising an N-(heterocyclicaminocarbonyl)arylsulfonamide herbicide present at a concentration inhibitory or lethal to normal cells; isolating mutant cell lines capable of sustained growth in the selective medium; and regenerating from the mutant cell lines reproductively competent plants that express resistance to said herbicide.

BRIEF DESCRIPTION OF THE DRAWINGS

FIG. 2 illustrates results of assays of acetolactate synthase activity in plant cell extracts derived from cell suspension cultures of a normal cell line (H1), and a mutual cell line (S4/S4), the latter being homozygous for the chlorsulfuron and sulfometuron methyl resistance trait. Extracts from each cell line were assayed following incubation with various concentrations of chlorsulfuron.

DETAILED DESCRIPTION OF THE INVENTION

Figure 1:
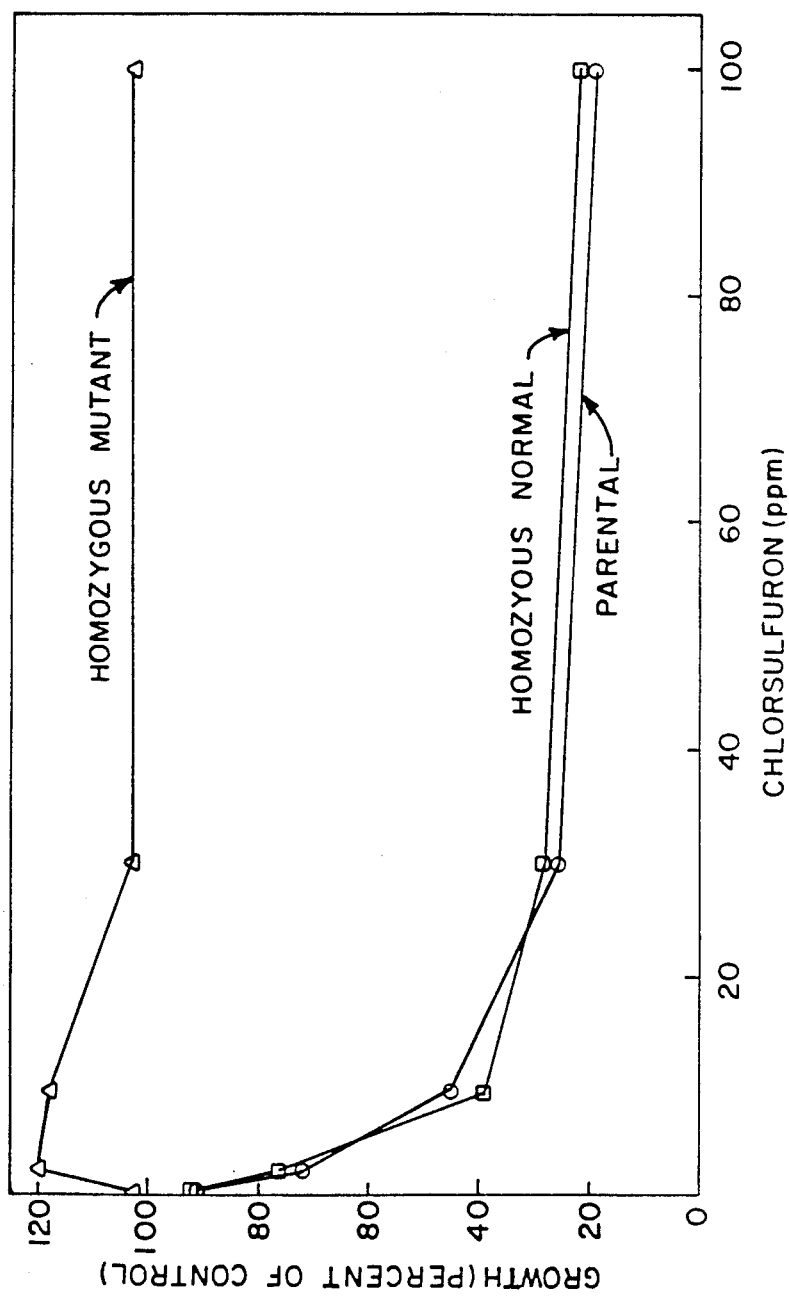
FIG. 1 depicts results of plant growth experiments involving progeny of plants regenerated from mutant cell lines resistant to sulfometuron-methyl and chlorsulfuron. The abscissal values represent averaged growth responses (measured as plant height) in the presence of chlorsulfuron, expressed as percentages relative to averaged growth response of control plants grown in the absence of chlorsulfuron.

This invention provides mutant *Nicotiana tabacum* plants exhibiting resistance to N-(heterocyclicaminocarbonyl)arylsulfonamide herbicides, as well as mutant tobacco genes, the presence of which in a *Nicotiana tabacum* plant permit expression of an altered acetolactate synthase enzyme which is insensitive to inhibition by N-(heterocyclicaminocarbonyl)arylsulfonamide herbicides.

Mutant plants and cell lines of the present invention exhibit cross-resistance to structurally related sulfonamide compounds effective as broad-spectrum preemergent and postemergent herbicides. As used herein, "herbicidally-effective sulfonamide compounds" means N-(heterocyclicaminocarbonyl)arylsulfonamide compounds exhibiting broad-spectrum herbicidal activity and low mammalian toxicity. These compounds can be described by reference to the following structural formulae, which are to be considered illustrative and not limiting with respect to the scope of sulfonamide herbicides useful in various embodiments of the present invention. Exemplary are compounds of the formulae

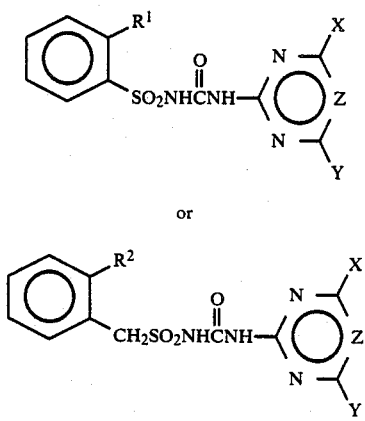

wherein
R$^1$ is Cl, CF$_3$, NO$_2$, C$_1$-C$_3$ alkyl, CO$_2$CH$_3$, CO$_2$C$_2$H$_5$, SCF$_2$H, SO$_2$R$^3$, OSO$_2$R$^3$, C$_1$-C$_3$ alkoxy, OCH$_2$CH=CH$_2$, or SO$_2$N(CH$_3$)$_2$;
R$^2$ is CO$_2$CH$_3$, CO$_2$C$_2$H$_5$, SO$_2$N(CH$_3$)$_2$, SO$_2$R$_3$ or NO$_2$;
R$_3$ is C$_1$-C$_3$ alkyl;
X is Cl, CH$_3$, or OCH$_3$;
Y is CH$_3$ or OCH$_3$; and
Z is CH or N;
provided that, when X is Cl, Z is CH; and when R$^1$ is SCF$_2$H, X is CH$_3$ or OCH$_3$.

Preferred sulfonamide herbicides include those in which R$^1$ is Cl, CO$_2$CH$_3$, CO$_2$C$_2$H$_5$, or OSO$_2$R$_3$; and those in which R$^2$ is CO$_2$CH$_3$ or CO$_2$C$_2$H$_5$.

Particularly preferred sulfonamide herbicides are chlorsulfuron, in which, in the foregoing formula A, R$^1$ is Cl, X is OCH$_3$, Y is CH$_3$ and Z is N; and sulfometuron-methyl, in which R$^1$ is CO$_2$CH$_3$, X and Y are each CH$_3$, and Z is CH. It will be apparent to those having skill in the art that a broad spectrum of herbicidally-effective sulfonamide compounds would be useful in the practice of various aspects of the present invention, and would thus be obvious equivalents of the compounds previously described. For the purposes of the present invention, such equivalents include, for example, the classes of herbicidal sulfonamide compounds disclosed by the following U.S. patents and published European patent applications:

| | |
|---|---|
| U.S. Pat. No. 4,169,719; | U.S. Pat. No. 4,231,784; |
| U.S. Pat. No. 4,127,405; | U.S. Pat. No. 4,394,506; |
| U.S. Pat. No. 4,190,432; | U.S. Pat. No. 4,383,113; |
| U.S. Pat. No. 4,225,337; | E.P. No. 23,422; |
| U.S. Pat. No. 4,257,802; | E.P. No. 44,212; and |
| U.S. Pat. No. 4,214,890; | E.P. No. 51,466. |
| U.S. Pat. No. 4,310,346; | |

Chlorsulfuron and sulfometuron methyl are the active ingredients in the two N-(heterocyclicaminocarbonyl)arylsulfonamide herbicides Glean ® and Oust ®, respectively, which are marketed by E. I. du Pont de Nemours & Company (Wilmington, Del., U.S.A.). *Nicotiana tabacum* mutants resistant to these compounds have been isolated from cell cultures. One such mutation, S4, increased resistance of plants to chlorsulfuron at least 100-fold when present in the homozygous state. Biochemical characterization of mutant plants has now revealed both the site of action of these herbicides and the mechanism by which resistance is effected.

The discovery that sulfometuron methyl inhibits growth of *Salmonella typhimurium* in the presence of valine and that this inhibition is reversed specifically by isoleucine first suggested that this herbicide acts by interfering with an early step in the biosynthesis of the branched-chain amino acids (LaRossa et al., *J. Biol. Chem.* 259:8753 (1984)). Similar patterns of reversal of growth inhibition were obtained with pea (*Pisum sativum*) and the yeast *Saccharomyces cerevisiae*. Growth inhibition by chlorsulfuron of pea seedlings and root cultures is prevented by supplementation of the medium with isoleucine and valine. Growth of yeast in the presence of sulfometuron methyl was restored by addition of isoleucine, leucine, and valine. (Falco et al., *Genetics* 109:21 (1985)). Direct assay of the first enzyme specific to the isoleucine-leucine-valine biosynthetic pathway, acetolactate synthase (ALS) (E.C.4.1.3.18) demonstrated the sensitivity of the ALS activities of these three organisms and of tobacco to extremely low concentrations of chlorsulfuron and sulfometuron methyl.

However, demonstration of the sensitivity of an enzyme to a herbicide is necessary, but not sufficient, evidence to identify the site of action of that herbicide. A possibility that is too often overlooked in such investigations is that the herbicide inhibits other enzymes in addition to the one identified (perhaps within the same metabolic pathway) and that it is primarily the action of the herbicide on one of these other activities that determines the response of the whole organism.

A particular enzyme can be established as the primary (or sole) site of action of a herbicide by a combination of genetic and biochemical lines of evidence that include demonstration that mutants resistant to a herbicide possess an altered form of an enzyme that is insensitive to the herbicide and that the resistant form of the enzyme cosegregates with the resistance phenotype in genetic crosses. The results of such experiments are reported below, which provide strong evidence that ALS is the site of action in tobacco of the N-(heterocyclicaminocarbonyl)arylsulfonamide herbicides chlorsulfuron and sulfometuron-methyl.

Methods of plant cell tissue culture, mutagenesis, regeneration of whole plants from callus cultures, and sexual crossing are known to those skilled in the art. Accordingly, these methods will be described only in general terms herein or by reference to specific embodiments of the invention set forth hereinafter. Further detail regarding various plant cell culture and genetic techniques can be found in Reinert et al., *Plant Cell and Tissue Culture* (Springer-Verlag, New York, 1982), Chaleff, *Genetics of Higher Plants: Applications of Cell Culture*, (Cambridge University Press, New York, 1981), and Street, ed., *Plant Tissue and Cell Culture* (University of California Press, Berkeley, 2nd ed. 1977).

In the practice of the present invention, cell cultures can be initiated under aseptic conditions from explants taken from diploid or haploid plants. As used herein, "cell cultures" means protoplasts, single cells, aggregates of cells, and callus tissue of either somatic or gametic origin propagated on solid or in liquid media. Preferably, the mutant selection method of the invention is carried out with haploid cells, which can be obtained by culturing anthers of *N. tabacum* under aseptic tissue culture conditions. Culture media employed in practicing the invention can be any suitable plant tissue culture media known to those skilled in the art. A number of useful media having been devised for culturing plant cells and protoplasts. A particularly useful medium for maintenance and propagation of cultured cells is referred to herein as "C1 medium". This medium is a culture medium disclosed by Linsmaier and Skoog, *Physiol. Plant* 18:100–127 (1965), supplemented with 3% (w/w) sucrose, 2.0 mg/L 1-naphthaleneacetic acid, and 0.3 mg/L kinetin. For callus cultures, 0.8% (w/w) agar can be added to C1 medium. The composition of Linsmaier and Skoog medium is set forth below:

| Linsmaier and Skoog Medium (pH = 6.2 before autoclaving) | | |
|---|---|---|
| Component | mg/L | g/L |
| $NH_4NO_3$ | 1650 | — |
| $KNO_3$ | 1900 | — |
| $CaCl_2.2H_2O$ | 440 | — |
| $MgSO_4.7H_2O$ | 370 | — |
| $KH_2PO_4$ | 170 | — |
| $Na_2EDTA$ | 37.3 | — |
| $FeSO_4.7H_2O$ | 27.8 | — |
| $H_3BO_3$ | 6.2 | — |
| $MnSO_4.H_2O$ | 16.9 | — |
| $ZnSO_4.7H_2O$ | 10.6 | — |
| KI | 0.83 | — |
| $Na_2MoO_4.2H_2O$ | 0.25 | — |
| $CuSO_4.5H_2O$ | 0.025 | — |
| $CoCl_2.6H_2O$ | 0.025 | — |
| Sucrose | — | 30.0 |
| Thiamine-HCl | 1.0 | — |
| Myo-Inositol | 100.0 | — |

Cell cultures are initiated by macerating leaves or other explant tissue from sterile plants on C1 medium.

Mutagenesis of cell cultures can be accomplished by use of various mutagens known in the art, e.g., X-rays, UV radiation, ethyl methane sulfate, nitrosoquanidine, ethyl nitrosourea, etc. In the case of ethyl nitrosourea, cell cultures can be maintained on C1 medium containing 0.1–3.0 mM ethyl nitrosourea for about 3 weeks prior to selection plating.

The resulting cell cultures are then transferred to suitable media, e.g., C1 medium, containing from about 0.5 to about 10 ppb (parts per billion by weight) of a selected herbicidally-effective sulfonamide compound. Such a medium is referred to herein as a "selective medium." Cultures are then incubated at about 25° C. under suitable artificial lighting. Cell lines arising from resistant cells appear, on average, between 1 and 2 months after plating. Two or more passages on selective media are preferably employed to confirm the presence and stability of resistant cell lines.

Plants are regenerated from callus cultures by transfer to shoot-induction media, which can be Linsmaier and Skoog medium containing 3% (w/w) sucrose, 0.3 mg/L indole-3-acetic acid and 3.0 mg/L 6-( , -dimethylallylamino)purine. Several passages on this medium, for about 3 weeks per passage, can be employed to induce shoot formation. Root formation can be accomplished by passage on Linsmaier and Skoog medium containing 3% (w/w) sucrose and 0.1 mg/L 1-naphthaleneacetic acid. The resulting plantlets are then grown to a height of 5–8 cm on hormone-free Linsmaier and Skoog medium containing 1% (w/w) sucrose, prior to transfer to sterile potting soil. Collectively, the foregoing shoot-induction and root-induction techniques, as well as other regenerative techniques known to those skilled in the art, are termed "regenerative procedures".

The various aspects and embodiments of the present invention are further illustrated by the following examples. All percentages are reported by weight and all temperatures in degrees Celcius unless otherwise indicated.

EXAMPLE 1

Isolation of Mutant Cell Lines

A haploid individual plant, herein designated "H1", was obtained by culturing anthers of *Nicotiana tabacum* cv. Xanthi according to the method of Nitsch, et al., *Science* 163:85 (1969). Explant tissue from young leaves of H1 was used to initiate callus cultures. Resistant cell lines were selected after transferring callus cells to C1 medium containing 2 ppb (about $5.6 \times 10^{-9}$ M) chlorsulfuron or sulfometuron-methyl. Several populations of callus cells were maintained in C1 medium containing 1 mM ethyl nitrosourea, a chemical mutagen, for about three weeks prior to initiation of the selection process.

Resistant cell lines appearing on selection plates were propagated on selective media for two additional passages of approximately 3 weeks each, and the resulting resistant cell lines were regenerated substantially in accordance with the general procedure previously described. Ten individual isolates were chosen for further study, five of which were selected for resistance to chlorsulfuron (C1, C2, C3, C4, C5) and five for resistance to sulfometuron-methyl (S1, S4, S5, S6, S7). Isolates C3 and C4 were obtained from mutagenically treated cell cultures.

EXAMPLE 2

Genetic Characterization of Plants Regenerated from Resistant Isolates

A fertile plant regenerated from isolate S4 substantially according to the procedure previously described was used in a series of crosses designed to evaluate the nature of the mutation or mutations conferring resistance to sulfometuron-methyl. Normal plants (N) were grown from seeds of the parent strain from which all mutant isolates were derived.

In growth experiments, seeds were surface-sterilized by immersion for 15 minutes in a solution containing about 0.5% sodium hypochlorite and about 0.1% sodium dodecyl sulfate. After rinsing with sterile distilled water, the seeds were germinated on control and selective media containing one-half the concentration of salts disclosed by Murashige, et al., *Physiol. Plant* 15:473 (1962), 100 mg/L myo-inositol, 10 g/L sucrose, and 16 g/L potato dextrose agar. Selective media contained 200 ppb sulfometuron-methyl.

The results of crosses and growth experiments involving isolate S4 and its progeny are presented in Table 1, below. "N" designated the parent, or normal, strain, and "R" a regenerated plant derived from isolate S4. The pattern of segregation indicated that the plant regenerated from isolate S4 was homozygous for a single dominant nuclear mutation conferring resistance to sulfometuron-methyl.

TABLE 1

Segregation among progeny of crosses with a mutant S4 regenerated plant (R).

| | Number of Individuals | | | |
|---|---|---|---|---|
| | Resistant | | Sensitive | |
| Cross | Observed | Expected | Observed | Expected |
| N selfed | 0 | | 459 | |
| R selfed | 176 | | 0 | |
| R × N | 311 | | 0 | |
| N × R | 52 | | 0 | |
| (R × N) × N | 39 | 38 | 37 | 38 |
| (R × N) selfed | 100 | 100.5 | 34 | 33.5 |

A similar series of crosses with plants regenerated from other isolates (S1, S4, S5, S6, S7, C1, C2, C3, C4 and C5) established that in these cases resistance likewise resulted from single dominant or semidominant nuclear mutations. Plants regenerated from only one isolate (C3) were heterozygous. Apparently, a mutation conferring resistance upon isolate C3 arose after diploidization of a haploid cell of the parental H1 cell line. In all other cases, mutations apparently occurred either in a haploid cell that subsequently diploidized or in a diploid cell in which homozygosity was restored by somatic recombination.

Genetic analysis of mutant S4 was further pursued by self-fertilizing a heterozygous plant produced by two successive backcrosses of the regenerated mutant plant to normal plants. Callus cultures established from the resulting progeny were tested for growth on medium supplemented with sulfometuron-methyl. In addition, seeds produced by self-fertilization of these plants were germinated on herbicide-supplemented medium. All 45 progeny of the S4/+ heterozygote that produced resistant callus cultures also produced resistant progeny. Only sensitive seed were obtained from 17 progeny that gave rise to sensitive callus cultures. Cosegregation of resistances of derivative callus cultures and of seedlings indicated that resistance at both levels of differentiation resulted from the same mutation. Self-fertilization of progeny of the S4/+ heterozygote also enabled homozygous and heterozygous individuals to be distinguished. Of 62 progeny examined in this manner, 16 proved to be homozygous mutant, 29 heterozygous and 17 homozygous normal plants. These results were consistent with an expected segregation ratio of 1:2:1.

Linkage analysis of 6 mutations was performed by first crossing two homozygous mutant plants to construct individuals heterozygous for two mutant alleles. These doubly heterozygous plants were then crossed with normal plants. If two mutations are allelic (or closely linked) only resistant progeny will be obtained from the testcross. However, if two mutations are unlinked, one-fourth of the progeny of the testcross will be sensitive. The linkage data presented in Table 2, below, established that the 6 mutations were located in two distinct genetic regions and therefore represented at least that number of genetic loci. Mutations S1, S5, S6 and C3 define one region and mutations S4 and C4 define a second region.

TABLE 2

Linkage Analysis

| | Number of Individuals | | | |
|---|---|---|---|---|
| | Resistant | | Sensitive | |
| Cross | Observed | Expected | Observed | Expected |
| +/+ × (S1/S1 × S6/S6) | 109 | | 2[a] | |
| (S1/S1 × S6/S6) × +/+ | 54 | | 2[a] | |
| +/+ × (S1/S1 × S5/S5) | 109 | | 6[a] | |
| (S1/S1 × S5/S5) × +/+ | 58 | | 1[a] | |
| +/+ × (S4/S4 × S1/S1) | 42 | (41.25) | 13 | (13.75) |
| (S4/S4 × S1/S1) × +/+ | 93 | (91.5) | 29 | (30.5) |
| +/+ × (S5/S5 × S6/S6) | 38 | | 0 | |
| (S5/S5 × S6/S6) × +/+ | 61 | | 0 | |
| (S5/S5 × S4/S4) × +/+ | 22 | (29.25) | 17 | (9.75) |
| +/+ × (C3/C3 × S4/S4) | 78 | | 25 | |
| (C3/C3 × S4/S4) × +/+ | 212 | | 80 | |
| (C3/C3 × S5/S5) × +/+ | 220 | | 7[a] | |
| +/+ × (C4/C4 × C3/C3) | 211 | (215.25) | 76 | (71.75) |
| +/+ × (C4/C4 × S6/S6) | 48 | (44.25) | 11 | (14.75) |
| (C4/C4 × S6/S6) × +/+ | 39 | (40.5) | 15 | (13.5) |
| +/+ × (S4/S4 × C4/C4) | 50 | | 0 | |
| (S4/S4 × C4/C4) × +/+ | 120 | | 0 | |
| (S5/S5 × C4/C4) × +/+ | 58 | (60) | 22 | (20) |

[a]Similar numbers of poorly growing individuals were observed among control populations plated on nonselective medium. Therefore, these "sensitive" individuals probably did not represent either independent assortment or recombination between two mutations, but segregation of an independent lethal mutation unrelated to seedling response to herbicide.

No recessive mutations were observed in the foregoing experiments. Because parental cell line H1 was initiated from a haploid plant and all but one of the mutants recovered were homozygous, presumably the isolation of recessive mutations was possible in this system. It appears, therefore, that either there is no mechanism by which resistance to these herbicides can be achieved by a recessive mutation or that such mutations are obtained at a much lower frequency than dominant mutations.

All resistant isolates that were analyzed genetically proved to be true mutants. That is, in all cases resistance was transmitted through sexual crosses in accord with conventional inheritance patterns. Moreover, in all cases, the resistance phenotype was expressed during both callus and seedling stages.

EXAMPLE 3

Evaluation of Resistance Phenotype at the Cellular Level

To evaluate the resistance of mutant cell lines to sulfonamide herbicides, a series of callus growth tests were conducted. Although the S4 mutation was selected on the basis of resistance to sulfometuronmethyl, preliminary studies indicated that the S4 mutation conferred a higher degree of resistance to chlorsulfuron. Accordingly, chlorsulfuron was employed in callus growth tests. As previously noted, these two herbicidally-effective sulfonamide compounds are structurally analogous; thus, the cross resistance observed was not unexpected.

Experiments designed to evaluate cosegregation of resistances to chlorsulfuron and sulfometuron-methyl demonstrated that both resistances are the result of mutations within the same genetic locus. In these experiments, callus cultures were established from 34 progeny of a testcross of an S/4+ heterozygote. Eight of the resulting callus cultures were resistant, and 16 sensitive, to both herbicides. No culture was observed to be independently resistant to either one or the other herbicide.

Callus growth tests were conducted substantially according to the following procedure. Approximately 50 mg callus tissue, grown on non-selective media, was spread over 7 cm diameter paper filter discs (Whatman No. 1), which were placed on the medium surface of petri dishes containing C1 agar media and varying concentrations of chlorsulfuron. The resulting cultures were incubated for 14 days at 25±1°, under fluorescent lamps programmed to provide a 16-hour photoperiod per day. At the conclusion of the incubation period, tissue was scraped from each filter disc and weighed. The final fresh weights were recorded, and means and standard errors of the means determined for all cases. These data are presented in Table 3, below. The significance of differences between responses of individual cell lines to various concentrations of chlorsulfuron was determined at a probability level of 5% by a t-test for populations having different standard deviations, as described by Snedecor, et al., *Statistical Methods* (Iowa State University Press, Ames, Iowa, (1967), pp. 114–116).

The isolates tested were established from plants produced by self-fertilization of a S4/+ heterozygote produced by two successive backcrosses of a regenerated mutant plant to normal plants. In addition, growth responses were determined for cell cultures initiated from two individuals of the same genotype with respect to the S4 mutation. The genotypes of these cell lines were confirmed by progeny analyses of the plants from which they were derived. These precautions were intended to eliminate background variability which might otherwise obscure the effects of the resistance mutation.

TABLE 3

Growth responses to chlorsulfuron of cell lines derived from isolates produced by self-fertilization of an S4/+ heterozygote

| Chlorsulfuron (ppb) | Isolate 1 (+/+) | | | Isolate 7 (+/+) | | |
|---|---|---|---|---|---|---|
| | Fr. Wt. (mg) | % | b | Fr. Wt. (mg) | % | n |
| 0 | 2982 ± 173 | 100 | 10 | 2332 ± 111 | 100 | 10 |
| 0.1 | 2287 ± 198 | 76.7 | 10 | 2170 ± 94 | 93.1 | 10 |
| 0.3 | 1204 ± 107 | 40.4 | 9 | 1395 ± 116 | 59.8 | 8 |
| 1.0 | 106 ± 9 | 3.6 | 9 | 215 ± 33 | 9.2 | 10 |
| 3.0 | 55 ± 3 | 1.8 | 9 | 58 ± 4 | 2.5 | 10 |
| 10.0 | | | | | | |
| 30.0 | | | | | | |

| Chlorsulfuron (ppb) | Isolate 23 (S4/+) | | | Isolate 24 (S4/+) | | |
|---|---|---|---|---|---|---|
| | Fr. Wt. (mg) | % | n | Fr. Wt. (mg) | % | n |
| 0 | 2670 ± 115 | 100 | 25 | 2874 ± 164 | 100 | 22 |
| 0.1 | 2803 ± 153 | 105.0 | 10 | 2895 ± 187 | 100.7 | 16 |
| 0.3 | 2559 ± 174 | 95.8 | 20 | 2842 ± 124 | 98.9 | 19 |
| 1.0 | 2505 ± 134 | 93.8 | 18 | 2515 ± 155 | 87.5 | 10 |
| 3.0 | 2401 ± 218 | 89.9 | 10 | 2099 ± 129 | 73.0 | 18 |
| 10.0 | 1537 ± 90 | 57.6 | 15 | 2196 ± 235 | 76.4 | 12 |
| 30.0 | 749 ± 54 | 28.1 | 15 | 1585 ± 129 | 55.1 | 12 |

| Chlorsulfuron (ppb) | Isolate 16 (S4/S4) | | | Isolate 30 (S4/S4) | | |
|---|---|---|---|---|---|---|
| | Fr. Wt. (mg) | % | n | Fr. Wt. (mg) | % | n |
| 0 | 3286 ± 198 | 100 | 18 | 2752 ± 205 | 100 | 10 |
| 0.1 | 3755 ± 259 | 114.3 | 10 | 3235 ± 159 | 117.6 | 10 |
| 0.3 | 3778 ± 219 | 115.0 | 12 | 3157 ± 76 | 114.7 | 8 |
| 1.0 | 3148 ± 196 | 95.8 | 13 | 2707 ± 250 | 98.4 | 10 |
| 3.0 | 2958 ± 161 | 90.0 | 11 | 3287 ± 136 | 119.4 | 10 |
| 10.0 | 3171 ± 260 | 95.5 | 18 | 2975 ± 139 | 108.1 | 10 |
| 30.0 | 2625 ± 202 | 79.9 | 17 | 2486 ± 170 | 90.3 | 10 |

As the data in Table 3 indicate, differences were observed between the growth responses of cell lines derived from individuals of the same genotype with respect to the S4 mutation. For example, growth of one normal cell line (Isolate 1) was significantly inhibited by 0.1 ppb chlorsulfuron, whereas growth of the other normal cell line (Isolate 7) was not. Isolate 1 appeared in general to be more sensitive to chlorsulfuron than Isolate 7. In contrast, the two homozygous mutant cell lines responded similarly to chlorsulfuron. Growth of neither homozygous mutant cell was significantly inhibited by concentrations of chlorsulfuron below 30 ppb. Because growth of the homozygous mutant lines is less severly affected by 30 ppb chlorsulfuron than is growth of the cell line derived from Isolate 7 (the mroe tolerant of the two normal lines) by 0.3 ppb, it appears that the S4 mutation in a homozygous state increases the tolerance of cultured cells for chlorsulfuron at least 100-fold. Both heterozygous lines were more sensitive to the herbicide than the homozygous mutant lines, particularly at higher concentrations. This result indicated that the S4 mutation was semidominant.

EXAMPLE 4

Evaluation of Cross-Resistance

A series of experiments was performed to investigate further the cross-resistance of various resistant cell lines to other herbicidally-effective sulfonamides. First, several homozygous mutant cell lines were evaluated for resistance to sulfometuron-methyl and chlorsulfuron by callus growth tests, performed substantially similarly to the callus growth experiments previously described. In these experiments, callus cultures were derived from R1 plants, which constitute the progeny produced by self-fertilization of a regenerated plant. The results of these tests are set forth in Table 4, below.

TABLE 4

Relative resistances of several homozygous mutant cell lines to sulfometuron-methyl and chlorsulfuron.

| | Control | | 10 ppb Sulfometuron-methyl | | | 10 ppb Chlorsulfuron | | |
|---|---|---|---|---|---|---|---|---|
| | Fr. Wt. | n | Fr. Wt. | % | n | Fr. Wt. | % | n |
| H1 | 2573 ± 126 | 7 | 32 ± 2 | 1.2 | 9 | 33 ± 2 | 1.3 | 9 |
| S1/S1 | 2676 ± 90 | 8 | 172 ± 14 | 6.4 | 10 | 309 ± 34 | 11.5 | 10 |
| S4/S4 | 3286 ± 198 | 18 | 1105 ± 80 | 33.6 | 15 | 3171 ± 260 | 96.5 | 18 |
| S5/S5 | 2639 ± 129 | 8 | 344 ± 55 | 13.0 | 10 | 725 ± 95 | 27.5 | 10 |
| S6/S6 | 3348 ± 159 | 9 | 887 ± 92 | 26.5 | 10 | 1076 ± 108 | 32.1 | 10 |
| C3/C3 | 2186 ± 165 | 8 | 1369 ± 63 | 62.6 | 10 | 1896 ± 119 | 86.7 | 10 |

TABLE 4-continued

Relative resistances of several homozygous mutant cell lines to sulfometuron-methyl and chlorsulfuron.

| | Control | | 10 ppb Sulfometuron-methyl | | | 10 ppb Chlorsulfuron | | |
|---|---|---|---|---|---|---|---|---|
| | Fr. Wt. | n | Fr. Wt. | % | n | Fr. Wt. | % | n |
| C4/C4 | 4137 ± 254 | 9 | 3473 ± 323 | 83.9 | 10 | 3453 ± 231 | 83.5 | 10 |

The results presented in Table 4 indicate phenotypic differences between callus cultures derived from different mutant isolates, as revealed by their relative resistances to chlorsulfuron and sulfometuron-methyl. Mutant S4 appears to be more resistant to chlorsulfuron than to sulfometuron-methyl, the compound on which it was isolated. Mutant C4, which was genetically linked to S4, but was independently selected on the basis of resistance to chlorsulfuron, displayed the same high degree of resistance to both compounds. Although mutants S1, S4, S5, and S6 were isolated in the same experiment, the different degrees of resistance exhibited by these mutants suggest that each mutation arose independently. No correlation was apparent between the resistance phenotypes of the mutants and their genetic linkage relationships.

The phenomenon of cross-resistance was also investigated by callus growth tests of a cell line homozygous for the S4 mutation, in the presence of six herbicidally effective sulfonamide compounds (chlorsulfuron and compounds A-E). These compounds vary with respect to substituents $R^1$, X, Y, and Z, as set forth in the following formula and table.

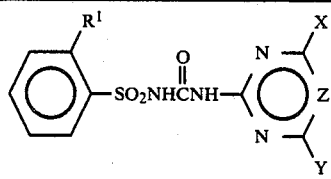

| | Substituents | | | |
|---|---|---|---|---|
| Compound | $R^1$ | X | Y | Z |
| Chlorsulfuron | Cl | $OCH_3$ | $CH_3$ | N |
| Sulfometuron-methyl | $CO_2CH_3$ | $CH_3$ | $CH_3$ | CH |
| A | Cl | $CH_3$ | $CH_3$ | CH |
| B | Cl | $CH_3$ | $OCH_3$ | CH |
| C | Cl | $OCH_3$ | $OCH_3$ | CH |
| D | Cl | $CH_3$ | $CH_3$ | N |
| E | Cl | $OCH_3$ | $OCH_3$ | N |

In these growth tests, petri dishes containing C1 agar medium and 10 ppb of the sulfonamide herbicide chlorsulfuron and Compounds A through E were prepared. A sterile filter paper disc was placed in the center of each plate, and inoculated with 250 mg of callus tissue homozygous for the S4 mutation, or callus tissue derived from the haploid parent H1. The resulting cultures were incubated at 25° in the dark for 2 weeks. At the conclusion of the incubation period, filter discs containing callus cells were removed from culture dishes, placed on a Buchner funnel, and gentle suction applied to remove excess water. The resulting callus mass was then carefully scraped from the filter disc and weighed. Four replicates were included in each experiment.

The results of these tests, which are presented in Table 5, below, indicated that the haploid parent cell line was extremely sensitive to each sulfonamide herbicide compound tested. In contrast, callus tissue homozygous for the S4 mutation was completely resistant to each compound at a test concentration of 10 ppb.

TABLE 5

| Growth Response of S4/S4 Callus in the Presence of Chlorsulfuron and Structural Analogues | | |
|---|---|---|
| | Mean Fresh Weight (g) | |
| Compound | H1 (parent) | S4/S4 |
| Control | 4.92 | 5.46 |
| A | 0 | 5.16 |
| B | 0 | 5.60 |
| C | 0 | 5.08 |
| D | 0 | 4.53 |
| Chlorsulfuron | 0 | 4.42 |
| E | 0 | 4.97 |

EXAMPLE 5

Evaluation of Resistance at the Whole Plant Level

The first indication that mutations selected at the cellular level for resistance to chlorsulfuron and sulfometuron-methyl were expressed by the whole plant was provided by a seedling growth assay used in scoring crosses. Sensitive seeds germinated on selective medium but the resulting embryos were bleached and did not develop roots or leaves. In contrast, resistant seedlings were green and developed normally on this medium, albeit at a somewhat slower rate than in the absence of herbicide.

Further studies of the effect of the S4 mutation on whole plant response to chlorsulfuron were conducted with plants of the parental variety and progeny of homozygous mutant and homozygous normal isolates (Nos. 16 and 1, respectively) of the previously described backcross program. Accordingly, plants of the latter two types were derived, but separated by four generations, from the initial S4 mutant plant regenerated from callus culture.

Plants at the 4-5 leaf stage were treated with foliar sprays of an aqueous solution containing 10% (v/v) acetone, 0.2% polyoxyethylene sorbitan monolaurate (Tween 20), and 1, 3, 10, 30 or 100 ppm chlorsulfuron. Each plant received 5 mL of a spray solution. Two weeks after treatment, plants were evaluated for phytotoxicity and shoot heights were measured. Both parental and homozygous normal plants developed symptoms of phytotoxicity in response to 1 ppm chlorsulfuron treatment. At this lowest level of application, apical buds and youngest leaves of these sensitive plants were chlorotic. At 3 ppm, chlorosis was more severe and growth retardation readily apparent. These symptoms were more pronounced with increasing chlorsulfuron concentrations. Sensitive plants treated with 100 ppm chlorsulfuron showed extreme growth inhibition, chlorosis, and necrosis. In contrast, homozygous mutant plants were unaffected by treatment with chlorsulfuron, even at the highest test concentration of 100 ppm.

FIG. 1 illustrates variation in growth response exhibited by progeny of Isolates 1 and 16 in the presence of chlorsulfuron. Each point represents an average height of 4 plants. "Parental" indicated plants grown from seeds of the *N. tabacum* cv. Xanthi line from which all cell cultures were established. Average heights of untreated control plants are set forth below:

| | |
|---|---|
| Parental | 11.1 ± 0.8 cm |
| Normal | 10.1 ± 0.7 cm |
| Mutant | 9.2 ± 0.8 cm. |

EXAMPLE 6

Selection of Highly Resistant Cell Lines

Cell cultures initiated from a homozygous S4/S4 tobacco plant were transferred to medium supplemented with 200 ppb sulfometuron-methyl, a concentration that completely inhibits growth of the S4/S4 mutant cell line. Resistant colonies were selected as they appeared and transferred to medium containing this same elevated level of sulfometuron-methyl. Several cell lines that continued to grow during subsequent passages in the presence of 200 ppb of the herbicide were isolated. A growth test performed with one of these cell lines (cell line A) revealed that it is capable of growth, albeit at a greatly reduced rate, in the presence of a concentration of sulfometuron-methyl that is 1000 times the concentration that completely inhibits growth of a normal cell line (Table 6). A large part of this resistance is the result of the S4 mutation, for which this cell line is homozygous. However, because cell line A is inhibited by 100 ppb sulfometuron-methyl to approximatey the same degree as its parent S4/S4 is inhibited by 10 ppb, it appears that the new event increased resistance ten-fold beyond that conferred by the S4/S4 genotype.

only herbicide-sensitive progeny, callus cultures derived from all plants that yielded resistant progeny and, therefore, that carried the S4 mutation were capable of growth on medium supplemented with either chlorsulfuron or sulfometuron-methyl at 5 parts per billion (ppg) (14 nM). Cell suspension cultures were initiated from these callus cultures and from the parental haploid cell line (H1) by transferring callus to a liquid C1 medium in which 2,4-dichlorophenoxyacetic acid (2 mg/L) had been substituted for napthaleneacetic acid and from which agar had been omitted. ALS activity was then assayed in extracts prepared from these cell suspension cultures as follows.

Cell suspension cultures of normal (H1) and homozygous mutant (Isolate 16) cell lines were washed in C1 liquid medium. After washing, cells were extracted in a 100 mM potassium phosphate buffer (pH 7.5) containing 0.5 mM $MgCl_2$, 1 mM sodium pyruvate, 0.5 mM thiamine pyrophosphate, 10 micromolar flavine-adenine dinucleotide (FAD) and 10 percent (by volume) glycerol. Polyclar AT (BDH Chemicals Ltd) was added to a final concentration of 250 mg per gram fresh weight of tissue. After centrifugation at 27,000xg for 15 minutes at 4°, an equal volume of a saturated solution of amminium sulfate was added to the supernatant fraction. The resultant precipitate (representing a 0 to 50 percent ammonium sulfate fraction) was redissolved in 100 mM potassium phosphate buffer (pH 7.5) containing 0.5 mM $MgCl_2$, 1 mM sodium pyruvate, and salts were removed by passage through a Sephadex G-25 (Pharmacia PD-10) column.

ALS activity was assayed in a total volume of 500 microliters containing 100 microliters of the column eluate, 65 mM potassium phosphate buffer (pH 7.5) containing 10 mM $MgCl_2$, 40 mM sodium pyruvate, 250 micromolar thiamine pyrophosphate, 23 micromolar FAD, and 1, 5, 10, 50, 100, 500 or 1000 ppb chlorsulfuron or sulfometuron-methyl. After incubation at 30° for

TABLE 6

| Growth responses to sulfometuron-methyl of normal, homozygous S4/S4, and highly resistant tobacco cell lines | | | | | | | | | | | | | | |
|---|---|---|---|---|---|---|---|---|---|---|---|---|---|---|
| | Sulfometuron-Methyl Concentration | | | | | | | | | | | | | |
| | 0 | | 1 ppb | | | 10 ppb | | | 100 ppb | | | 1000 ppb | | |
| Cell Line | Fr. wt. (mg) | n | Fr. wt. (mg) | % | n | Fr. wt. (mg) | % | n | Fr. wt. (mg) | % | n | Fr. wt. (mg) | % | n |
| Normal (H1) | 2876 ± 161 | 10 | 39 ± 2 | 1.4 | 10 | 29 ± 1 | 1.0 | 10 | — | | | — | | |
| S4/S4 | 3286 ± 198 | 18 | — | | | 1105 ± 80 | 34 | 15 | — | | | — | | |
| "A" | 2651 ± 77 | 10 | 2379 ± 243 | 90 | 10 | 1952 ± 133 | 74 | 10 | 629 ± 72 | 24 | 10 | 263 ± 83 | 10 | 10 |

EXAMPLE 7

Demonstration that Acetolactate Synthase is the Site of Action of N-(heterocyclicaminocarbonyl)arylsulfonamide Herbicides in Tobacco A plant heterozygous for the S4 mutation was constructed by a series of backcrosses of a plant regenerated from a herbicide-resistant tobacco cell line with plants of the parental variety (*N. tabacum* cv. Xanthi). Self-fertilization of this heterozygous individual yielded homozygous mutant, heterozygous, and homozygous normal progeny in the ratio of 1 to 2 to 1, respectively, which is expected for segregation of a single semidominant nuclear allele. The genotypes of these progeny plants were confirmed by analysis of a subsequent generation. Callus cultures were established as previously described from several of the genetically defined isolates produced by self-fertilization of the S4/+ heterozygote. Unlike normal *N. tabacum* callus cultures and callus cultures initiated from segregants that produced 90 minutes, 250 microliters of 6N $H_2SO_4$ was added to each assay tube, and the tubes were incubated at 55° for 10 minutes to terminate the enzymatic reaction and achieve complete conversion of acetolactate to acetoin. Acetoin content was then measured by a modification of the procedure described by Westerfield, *J. Biol. Chem.* 161:495 (1945). To each tube was added sequentially 100 microliters 50 percent NaOH, 150 microliters 0.5 percent creatine, and 150 microliters 5 percent alpha-napthol (in 2.5N NaOH). Color development was accelerated by incubation at 55° for 10 minutes. Tubes were then centrifuged, and the optical density was read at 530 nm. Background optical densities, which were subtracted from the optical density values of the reactions, were determined for each extract from parallel assays to which the enzyme extract was added after the addition of 6N $H_2SO_4$. Protein concentrations were measured with Bio-Rad Protein Assay reagent with bovine serum albumin as a standard. Data points and specific activities, which are set forth below and in FIG. 2, represent the average values of at least three independent determinations. ALS activities are presented in FIG. 2 as percent activity in the absence of herbicide.

The specific activities of ALS in H1 extracts and in extracts of a homozygous mutant (Isolate 16) cell line were 161 and 168 nmole of acetoin per milligram of protein per hour, respectively. ALS activity of the H1 cell line was inhibited 50 percent by chlorsulfuron at approximately 5 ppb (14 nM). In contrast, this degree of inhibition of ALS activity in extracts of the mutant was not achieved by chlorsulfuron at 3000 ppb (8 micromolar), the highest concentration tested. ALS activity of the mutant cell line was also more resistant than the parental activity to inhibition by sulfometuron-methyl. However, the mutant activity displayed a higher degree of resistance to the former than to the latter compound, as indicated in FIG. 2. The relative resistances of ALS activity in the S4/S4 extract to chlorsulfuron and sulfometuron-methyl corresponded to the growth responses of this cell line to these two compounds. Growth of this same homozygous mutant cell line was inhibited 64 percent by sulfometuron-methyl at 10 ppb (28 nM) and less than 5 percent by chlorsulfuron at 10 ppb. This correspondence between the relative responses of mutant cell cultures and ALS activities in cell-free extracts indicates that an altered ALS enzyme provides the basis for the resistance phenotype.

Responses to chlorsulfuron were determined for ALS activities in extracts of cells suspension cultures derived from nine individuals that differed with resepct to the S4 mutation. As described above, these individuals were produced by self-fertilization of an S4/+ heterozygote, and their genotypes were established by means of progeny analysis. Callus and plant phenotypes were determined by growth responses of cell cultures and seedlings, respectively, on herbicide-supplemented medium. All normal, sensitive segregants had a chlorsulfuron-sensitve form of ALS that was indistinguishable from that of the parent H1 cell line. In contrast, all individuals homozygous for the S4 mutation contained a highly resistant form of the enzyme. The ALS activities in extracts of heterozygotes displayed an intermediate degree of resistance to chlorsulfuron, as indicated in Table 7, below. The correlation between both callus and plant phenotype and the response of ALS activity in vitro to the herbicide is both absolute and quantitative. The maintenance through genetic crosses of an association between the responses of the plant, cell culture, and ALS activity to chlorsulfuron indicates that this enzyme is the site of action of the N-(heterocyclicaminocarbonyl)arylsulfonamide herbicides in tobacco and that production of an insensitive form of the enzyme is the basis for resistance in the mutant.

The S4 mutation affecting production of an altered ALS enzyme insensitive to inhibition by N-(heterocyclicaminocarbonyl)arylsulfonamide herbicides may define the structural gene for this enzyme, or in the alternative, a regulatory gene which normally prevents expression of a more resistant ALS isozyme encoded in the tobacco genome.

Table 7, below, indicates sensitivity to chlorsulfuron of ALS activities in progeny of an S4/+ heterozygote. Data are presented as percent of ALS activity in the absence of chlorsulfuron. Each number represents the average of at least three independent experiments. Callus cultures initiated from the individual isolates were tested for growth on medium supplemented with chlorsulfuron at 5 ppb (14 nM). Callus cultures capable of growth on this medium are designated R (resistant). S denotes sensitive callus cultures that did not grow in the presence of the herbicide.

TABLE 7

Sensitivity to Chlorsulfuron of ALS Activities in Progeny of an S4/+ Heterozygote

| Isolate | Genotype | Callus Phenotype | Uninhibited activity (%) in the Presence of Chlorsulfuron | | |
|---|---|---|---|---|---|
| | | | 10 ppb | 30 ppb | 100 ppb |
| H1 | + | S | 40 | 23 | 18 |
| 1 | +/+ | S | 42 | 29 | 23 |
| 7 | +/+ | S | 36 | 22 | 16 |
| 9 | S4/+ | R | 59 | 50 | 42 |
| 10 | S4/+ | R | 61 | 52 | 45 |
| 16 | S4/S4 | R | 86 | 80 | 80 |
| 23 | S4/+ | R | 64 | 53 | 46 |
| 24 | S4/+ | R | 60 | 47 | 41 |
| 27 | S4/S4 | R | 88 | 82 | 79 |
| 30 | S4/S4 | R | 89 | 83 | 81 |

Production of Resistant First-Generation Hybrids

Incorporation of the homozygous resistant mutants of the present invention into a tobacco breeding program will permit production of first generation hybrid tobacco plants in which the sulfonamide herbicide resistance trait is expressed in combination with other agronomically valuable characteristics. These characteristics can relate, for example, to plant morphology, disease resistance, yield, pest resistance, drought or salt tolerance, or a variety of other important traits in tobacco.

Plant breeding techniques suitable for production of such first-generation hybrids are well-known to those skilled in the art. Such teqhniques are described in Poehlman, J. H., *Breeding Field Crops*, Henry Holt and Company, New York, (1959), and in Welsh, J. R., *Fundamentals of Plant Genetics and Breeding*, Wiley (1981). The disclosures of these volumes are herein incorporated by reference.

Production of Resistant Inbred Lines

A mutation conferring resistance to sulfonamide herbicides can be introduced into tobacco cultivars by means of a standard backcross breeding program. In such a program, a plant homozygous for the resistance mutation (donor parent) is crossed with an individual of the cultivar into which introduction of the resistance trait is desired (recurrent parent). The hybrid produced by this cross is then crossed with the recurrent parent. This process is repeated for several generations by crossing herbicide-resistant progeny of each successive cross with the recurrent parent until the resistance trait is combined in a true breeding (homozygous) form with the desirable traits of the recurrent parent).

Backcrossing programs are routinely used for the introduction of dominant resistant traits into inbred lines and are well known to those skilled in the art. Such techniques are described in Welsh, J. R., *Fundamentals of Plant Genetics and Breeding*, vide supra, and in Simmonds, N. W., *Principles of Crop Improvement*, Longman (1979).

Agronomic Use of Herbicide Resistant Tobacco

Methods of use of the resistant tobacco plants of the invention are in accordance with standard tobacco cultivation practices. Seed derived from resistant varieties, or hybrid seed produced in a breeding program involving resistant plants of the invention, can be planted in soils to which a selected sulfonamide herbicide has been applied at rates sufficient to prevent growth of undesired and adventitious species. Alternatively, the herbicide can be applied to fields of tobacco after plant emergence. The broad spectrum of effectiveness of sulfonamide herbicides can be expected to permit subsequent growth only of the resistant tobacco variety, to the near-complete exclusion of competing species. The potential savings in time, fuel and labor previously devoted to mechanical or manual cultivation, or repetitive applications of less effective herbicidal compositions, are readily apparent.

Deposit of Seed

A sample of viable seed from inbred homozygous resistance mutant Xanthi S4 has been deposited at the United States Department of Agriculture National Seed Storage Laboratory, Fort Collins, Colo., and has been assigned U.S. Ser. No. 182,037. In addition, reserve stock of viable seed representing embodiments of the present invention are maintained by the Central Research and Development Department, Research Division, E. I. du Pont de Nemours and Company (Inc.), Experimental Station, Wilmington, Del., to which all requests for seed samples should be directed.

What is claimed is:

1. A mutant *Nicotiana tabacum* plant having a mutation or mutations conferring resistance to soil concentrations or post-emergence applications of an N-heterocyclicaminocarbonyl)arylsulfonamide herbicide sufficient to kill *Nicotiana tabacum* plants not having said mutation or mutations, said plant being capable of transmitting said mutation or mutations to progeny by sexual reproduction.

2. A mutant *Nicotiana tabacum* plant according to claim 1, said plant having a mutation or mutations conferring resistance to an N-(heterocyclicaminocarbonyl)arylsulfonamide herbicide of the formula or wherein
$R^1$ is Cl, $CF_3$, $NO_2$, $C_1$-$C_3$ alkyl, $CO_2CH_3$, $CO_2C_2H_5$, $SCF_2H$, $SO_2R^3$, $OSO_2R^3$, $C_1$-$C_3$ alkoxy, $OCH_2CH=CH_2$, or $SO_2N(CH_3)_2$;
$R^2$ is $CO_2CH_3$, $CO_2C_2H_5$, $SO_2N(CH_3)_2$, $SO_2R_3$ or $NO_2$;
$R_3$ is $C_1$-$C_3$ alkyl;
X is Cl, $CH_3$, or $OCH_3$;
Y is $CH_3$ or $OCH_3$; and
Z is CH or N;
provided that, when X is Cl, Z is CH; and when $R^1$ is $SCF_2H$, X is $CH_3$ or $OCH_3$.

3. A mutant *Nicotiana tabacum* plant according to claim 2, said plant having a mutation or mutations conferring resistance to an N-(heterocyclicaminocarbonyl)arylsulfonamide herbicide of the formula or wherein
$R^1$ is Cl, $CO_2CH_3$, $CO_2C_2H_5$, or $OSO_2R^3$;
$R^2$ is $CO_2CH_3$ or $CO_2C_2H_5$; and
$R_3$ is $C_1$-$C_3$ alkyl;
X is Cl, $CH_3$, or $OCH_3$;
Y is $CH_3$ or $OCH_3$; and
Z is CH or N;
provided that, when X is Cl, Z is CH.

4. A mutant *Nicotiana tabacum* plant according to claim 3, said plant having a mutation or mutations conferring resistance to chlorsulfuron.

5. A mutant *Nicotiana tabacum* plant according to claim 3, said plant having a mutation or mutations conferring resistance to sulfometuron-methyl.

6. A mutant *Nicotiana tabacum* plant which expresses an altered acetolactate synthase enzyme insensitive to inhibition by N-(heterocyclicaminocarbonyl)arylsulfonamide herbicides, expression of said enzyme conferring resistance to growth inhibition of the plant by said herbicides.

7. A mutant *Nicotiana tabacum* plant according to claim 6 which expresses an altered acetolactate synthase enzyme insensitive to inhibition by an N-(heterocyclicaminocarbonyl)arylsulfonamide herbicide of the formula or wherein
$R^1$ is Cl, $CF_3$, $NO_2$, $C_1$-$C_3$ alkyl, $CO_2CH_3$, $CO_2C_2H_5$, $SCF_2H$, $SO_2R^3$, $OSO_2R^3$, $C_1$-$C_3$ alkoxy, $OCH_2CH=CH_2$, or $SO_2N(CH_3)_2$;

$R^2$ is $CO_2CH_3$, $CO_2C_2H_5$, $SO_2N(CH_3)_2$, $SO_2R_3$ or $NO_2$;

$R_3$ is $C_1-C_3$ alkyl;

X is Cl, $CH_3$, or $OCH_3$;

Y is $CH_3$ or $OCH_3$; and

Z is CH or N;

provided that, when X is Cl, Z is CH; and when $R^1$ is $SCF_2H$, X is $CH_3$ or $OCH_3$.

8. A mutant *Nicotiana tabacum* plant according to claim 7 which expresses an altered acetolactate synthase enzyme insensitive to inhibition by an N-(heterocyclicaminocarbonyl)arylsulfonamide herbicide of the formula

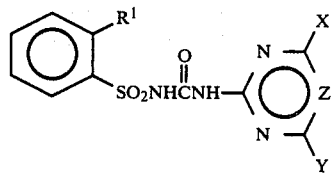

A or

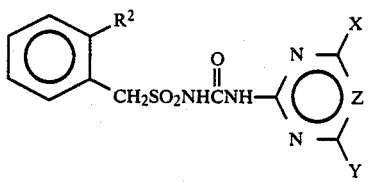

B wherein $R^1$ is Cl, $CO_2CH_3$, $CO_2C_2H_5$, or $OSO_2R^3$;

$R^2$ is $CO_2CH_3$ or $CO_2C_2H_5$; and $R_3$ is $C_1-C_3$ alkyl;

X is Cl, $CH_3$, or $OCH_3$;

Y is $CH_3$ or $OCH_3$; and

Z is CH or N;

provided that, when X is Cl, Z is CH.

9. A mutant *Nicotiana tabacum* plant according to claim 8 which expresses an altered acetolactate synthase enzyme insensitive to inhibition by chlorsulfuron.

10. A mutant *Nicotiana tabacum* plant according to claim 8 which expresses an altered acetolactate synthase enzyme insensitive to inhibition by sulfometuron-methyl.

11. A mutant *Nicotiana tabacum* plant according to claim 6, said plant having been produced by a process comprising:

(a) propagating cell cultures of *Nicotiana tabcum* under plant cell culture conditions;

(b) exposing the cell cultures to a selective medium comprising an N-(heterocyclicaminocarbonyl)arylsulfonamide herbicide present at a concentration inhibitory or lethal to normal cells;

(c) isolating mutant cell lines capable of sustained growth in the selective medium; and (d) regenerating from the mutant cell lines reproductively competent plants that express resistance to the herbicide.

12. A mutant *Nicotiana tabacum* plant according to claim 11, wherein the N-(heterocyclicaminocarbonyl)arylsulfonamide herbicide is a compound of the formula

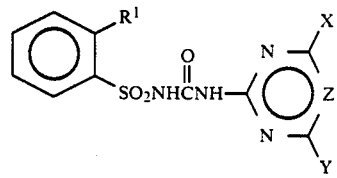

A or

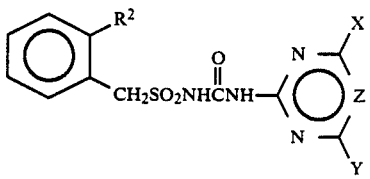

B wherein $R^1$ is Cl, $CF_3$, $NO_2$, $C_1-C_3$ alkyl, $CO_2CH_3$, $CO_2C_2H_5$, $SCF_2H$, $SO_2R^3$, $OSO_2R^3$, $C_1-C_3$ alkoxy, $OCH_2CH=CH_2$, or $SO_2N(CH_3)_2$;

$R^2$ is $CO_2CH_3$, $CO_2C_2H_5$, $SO_2N(CH_3)_2$, $SO_2R_3$ or $NO_2$;

$R_3$ is $C_1-C_3$ alkyl;

X is Cl, $CH_3$, or $OCH_3$;

Y is $CH_3$ or $OCH_3$; and

Z is CH or N;

provided that, when X is Cl, Z is CH; and when $R^1$ is $SCF_2H$, X is $CH_3$ or $OCH_3$.

13. A mutant *Nicotiana tabacum* plant according to claim 12, wherein the N-(heterocyclicaminocarbonyl)arylsulfonamide herbicide is a compound of the formula

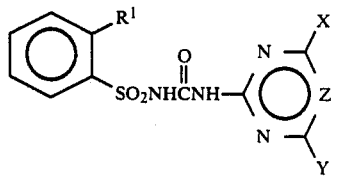

A or

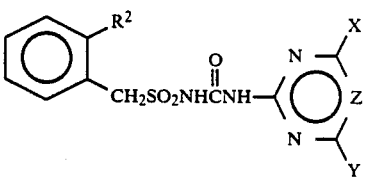

B wherein $R^1$ is Cl, $CO_2CH_3$, $CO_2C_2H_5$, or $OSO_2R^3$;

$R^2$ is $CO_2CH_3$ or $CO_2C_2H_5$; and $R_3$ is $C_1-C_3$ alkyl;

X is Cl, $CH_3$, or $OCH_3$;

Y is $CH_3$ or $OCH_3$; and

Z is CH or N;

provided that, when X is Cl, Z is CH.

14. A mutant *Nicotiana tabacum* plant according to claim 13, wherein the N-(heterocyclicaminocarbonyl)arylsulfonamide herbicide is chlorsulfuron.

15. A mutant *Nicotiana tabacum* plant according to claim 13, wherein the N-(heterocyclicaminocarbonyl)arylsulfonamide herbicide is sulfometuron-methyl.

16. A mutant *Nicotiana tabacum* gene, the presence of which in a *Nicotiana tabacum* plant permits expression of an altered acetolactate synthase enzyme which is insensitive to inhibition by N-(heterocyclicaminocarbonyl)arylsulfonamide herbicides.

17. A mutant *Nicotiana tabacum* gene according to claim 16, the presence of which in a *Nicotiana tabacum* plant permits expression of an altered acetolactate synthase enzyme which is insensitive to inhibition by an N-(heterocyclicaminocarbonyl)arylsulfonamide herbicide of the formula

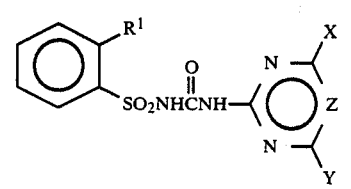

or

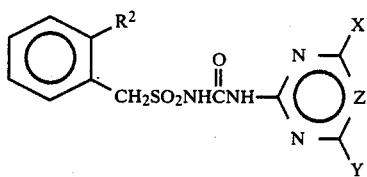

wherein
$R^1$ is Cl, $CF_3$, $NO_2$, $C_1$-$C_3$ alkyl, $CO_2CH_3$, $CO_2C_2H_5$, $SCF_2H$, $SO_2R^3$, $OSO_2R^3$, $C_1$-$C_3$ alkoxy, $OCH_2CH=CH_2$, or $SO_2N(CH_3)_2$;
$R^2$ is $CO_2CH_3$, $CO_2C_2H_5$, $SO_2N(CH_3)_2$, $SO_2R_3$ or $NO_2$;
$R_3$ is $C_1$-$C_3$ aklyl;
X is Cl, $CH_3$, or $OCH_3$;
Y is $CH_3$ or $OCH_3$; and
Z is CH or N;
provided that, when X is Cl, Z is CH; and when $R^1$ is $SCF_2H$, X is $CH_3$ or $OCH_3$.

18. A mutant *Nicotiana tabacum* gene according to claim 17, the presence of which in a *Nicotiana tabacum* plant permits expression of an altered acetolactate synthase enzyme which is insensitive to inhibition by an N-(heterocyclicaminocarbonyl)arylsulfonamide herbicide of the formula

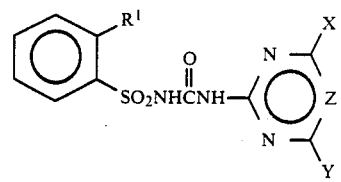

or

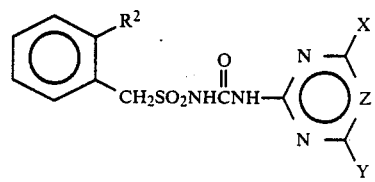

wherein
$R^1$ is Cl, $CO_2CH_3$, $CO_2C_2H_5$, or $OSO_2R^3$;
$R^2$ is $CO_2CH_3$ or $CO_2C_2H_5$; and
$R_3$ is $C_1$-$C_3$ alkyl;
X is Cl, $CH_3$, or $OCH_3$;
Y is $CH_3$ or $OCH_3$; and
Z is CH or N;
provided that, when X is Cl, Z is CH.

19. A mutant *Nicotiana tabacum* gene according to claim 18, the presence of which in a *Nicotiana tabacum* plant permits expession of an altered acetolactate synthase enzyme which is insensitive to inhibition by chlorsulfuron.

20. A mutant *Nicotiana tabacum* gene according to claim 18, the presence of which in a *Nicotiana tabacum* plant permits expression of an altered acetolactate synthase enzyme which is insensitive to inhibition by sulfometuron-methyl.

21. A hybrid tobacco seed which upon growth yeilds a tobacco plant having resistance to an N-(heterocyclicaminocarbonyl)arylsulfonamide herbicide, the hybrid seed having been produced by cross-pollinating parent plants, wherein at least one parent plant has gametes with nuclei which carry at least one dominant or semidominant gene conferring resistance to the N-(heterocyclicaminocarbonyl)arylsulfonamide herbicide.

* * * * *